US005681980A

United States Patent [19]

[11] Patent Number: 5,681,980
[45] Date of Patent: Oct. 28, 1997

Beerse et al.

[54] TOPPED, DISTILLED, COCOYL ISETHIONATE SKIN CLEANSING BAR

[75] Inventors: Peter William Beerse, Maineville; James Charles Dunbar, West Chester; Eddie Charles Walker, Cincinnati, all of Ohio

[73] Assignee: The Procter & Gamble Company, Cincinnati, Ohio

[21] Appl. No.: 531,799

[22] Filed: Sep. 21, 1995

Related U.S. Application Data

[63] Continuation of Ser. No. 148,733, Nov. 8, 1993, abandoned.

[51] Int. Cl.$^6$ .................................................. C07C 321/00

[52] U.S. Cl. ....................... 560/151; 252/367.1; 510/141; 510/152; 510/153

[58] Field of Search .................................... 252/549, 550, 252/551, 367.1; 510/141, 152, 153; 560/151

[56] References Cited

U.S. PATENT DOCUMENTS

| | | | |
|---|---|---|---|
| 2,894,912 | 7/1959 | Geitz | 252/121 |
| 4,007,125 | 2/1977 | Prince | 252/117 |
| 4,061,602 | 12/1977 | Oberstar et al. | 252/547 |
| 4,234,464 | 11/1980 | Morshauser | 252/544 |
| 4,472,297 | 9/1984 | Bolich et al. | 252/531 |
| 4,491,539 | 1/1985 | Hoskins et al. | 252/541 |
| 4,540,507 | 9/1985 | Grollier | 252/174.23 |
| 4,673,525 | 6/1987 | Small et al. | 252/132 |
| 4,704,224 | 11/1987 | Saud | 252/132 |
| 4,812,253 | 3/1989 | Small et al. | 252/132 |
| 4,820,447 | 4/1989 | Medcalf et al. | 252/117 |
| 4,861,507 | 8/1989 | Gervasio | 252/108 |
| 4,954,282 | 9/1990 | Rys et al. | 252/117 |
| 5,154,849 | 10/1992 | Visscher et al. | 252/174.15 |
| 5,204,014 | 4/1993 | Redd et al. | 252/117 |
| 5,264,144 | 11/1993 | Moroney et al. | 252/117 |
| 5,264,145 | 11/1993 | French et al. | 252/117 |

FOREIGN PATENT DOCUMENTS

| | | | |
|---|---|---|---|
| 472320A1 | 2/1992 | European Pat. Off. | A61K 7/50 |

OTHER PUBLICATIONS

*J. Invest. Dermatol.*, T. J. Franz, 175, 64, pp. 190–195.

*Primary Examiner*—Brian K. Burn
*Attorney, Agent, or Firm*—Tara M. Rosnell

[57] ABSTRACT

The present invention encompasses a personal cleansing bar comprising from 10 parts to 70 parts by bar weight of a distilled, topped $C_{12}$–$C_{18}$ acyl (topped cocoyl) isethionate (STCI). The bar of this invention contains little or no (0–2.8 parts) highly soluble acyl groups (sodium $C_6$, $C_8$, $C_{10}$, $C_{18:1}$ and $C_{18:2}$ acyl isethionate). The bar of this invention is mild, smells better than a bar made with ordinary sodium cocoyl isethionate (SCI), is more stable in terms of both odor and color, and is easier to make.

A preferred STCI bar contains a higher level of moisture without processing negatives which higher level of moisture contributes to better lather. The sodium topped cocoyl isethionate (STCI) also allows for an increase in levels of liquids and hygroscopic materials, in the bar formulation without the usual processing negatives.

11 Claims, No Drawings

TOPPED, DISTILLED, COCOYL ISETHIONATE SKIN CLEANSING BAR

This is a continuation of application Ser. No. 08/148,733, filed on Nov. 8, 1993 (now abandoned).

TECHNICAL FIELD

The present invention relates to personal cleansing bars containing acyl isethionate.

BACKGROUND OF THE INVENTION

Sodium acyl isethionate combo bars are, per se, old in the art, e.g., mild sodium acyl isethionate synthetic surfactant based personal cleansing bars are also disclosed in U.S. Pat. No. 2,894,912, July 1959, to Geitz and U.S. Pat. No. 4,954,282, Rys, et al., Sep. 4, 1990.

This invention relates to improved mild sodium acyl isethionate based skin cleansing toilet bars. In other words, this invention relates to skin cleansing toilet bars comprising sodium acyl isethionate as a primary synthetic surfactant.

The cleansing of skin with surface-active cleansing preparations has become a focus of great interest. Many athletic and socially conscious people wash and exfoliate their skin with various surface-active preparations several times a day. Ideal skin cleansers should cleanse the skin gently, causing little or no irritation, without defatting and overdrying the skin or leaving it taut after frequent routine use. Most lathering soaps, liquids and bars included, fail in this respect.

Synthetic detergent bars, frequently referred to as "combo bars" and/or "syndet bars," are known and are becoming increasingly popular. However, widespread replacement of soap bars by syndet bars has not so far been possible for a variety of reasons, primarily the poor physical characteristics of syndet bars as compared to soap bars, e.g., off odors, poor processability, stickiness, brittleness, smear or bar messiness, lather quality or combinations thereof.

One object of the present invention is to deliver a bar formulation that is mild to the skin; another object is to deliver a bar with reduced bar off odor; and yet another is to have a formulation that is easily processable.

SUMMARY OF THE INVENTION

The present invention encompasses a personal cleansing bar comprising at least 10 parts by bar weight of a sodium distilled, topped acyl (topped cocoyl) isethionate (STCI). The sodium topped cocoyl isethionate (STCI) of this invention contains little or no highly soluble $C_6$, $C_8$, $C_{10}$, $C_{18:1}$, $C_{18:2}$ acyl groups. The sodium topped cocoyl isethionate (STCI) of this invention contains from about 45% to 65% $C_{12}$, and from about 30% to about 55%, $C_{14}$, $C_{16}$ and $C_{18}$ acyl groups.

DETAILED DESCRIPTION OF THE INVENTION

The present invention encompasses a personal cleansing bar comprising 10 TO 70 parts by bar weight of a sodium distilled, topped acyl (topped cocoyl) isethionate (STCI). The STCI bar of this invention is also easier to make. The STCI bar of this invention is mild; it looks and smells better than a comparable bar made with ordinary sodium cocoyl isethionate (SCI).

The term "Sodium Topped Cocoyl Isethionate" or "STCI" as used herein mean that the cocoyl (acyl) groups have the following carbon chain lengths: from zero to 4% highly soluble acyl groups ($C_6$+$C_8$+$C_{10}$+$C_{18:1}$+$C_{18:2}$); from about 45% to 65% $C_{12}$, preferably 50–60% $C_{12}$; from about 30% to about 55%, preferably 35–50% $C_{14}$, $C_{16}$ and $C_{18}$.

Preferably any STCI highly soluble acyl groups ($C_6$, $C_8$, etc.) are from zero to below 3% of the total STCI. The low melting acyl isethionates are more preferably less than 2.8 parts by weight of the bar and are about zero when the total level of STCI is low.

The bar of this invention can be made more easily with a higher level of moisture without expected processing negatives. Increased bar moisture contributes to better bar lather. Use of the sodium topped cocoyl isethionate also allows for an increase in levels of other hygroscopics, such as alkyl glyceryl sulfonate (AGS) and alkyl ether(3) sulfate ($AE_3S$), in the bar formulation without exhibiting processing negatives that would otherwise be experienced using regular SCI.

More specifically, the STCI bar composition of this invention comprises the following components set out in Table A in parts by weight of the bar.

TABLE A

| Component in Parts | Full Range | Preferred | More Preferred |
|---|---|---|---|
| A. STCI | 10 to 70 | 15 to 60 | 20 to 50 |
| B. Na-Alkyl Glyceryl Ether Sulfonate | 0 to 50 | 5 to 30 | 10 to 20 |
| C. Na-Alkyl Ether Sulfate | 0 to 10 | 1 to 8 | 2 to 6 |
| D. Na-Cetearyl Sulfate | 0 to 40 | 4 to 30 | 8 to 20 |
| E. Na-soap | 0 to 20 | 1 to 15 | 2 to 12 |
| F. Mg-soap | 0 to 50 | 4 to 30 | 8 to 20 |
| G. Fatty Acid | 0 to 35 | 3 to 25 | 5 to 20 |
| H. Paraffin | 0 to 30 | 3 to 25 | 5 to 20 |
| I. NaCl | 0 to 5 | 0.1 to 3 | 0.2 to 2 |
| J. Na2SO4 | 0 to 5 | 0.1 to 3 | 0.2 to 2 |
| K. Na-Isethionate | 0 to 15 | 1 to 10 | 2 to 8 |
| L. Water | 3 to 20 | 4 to 15 | 5 to 10 |
| M. Fragrance | 0 to 2 | 0.5 to 1.5 | 0.8 to 1.2 |

A = Sodium Topped Cocoyl Isethionate (STCI). This ingredient is the key to the present invention. It is made from topped distilled coconut fatty acid.
B = Sodium Alkyl Glyceryl Ether Sulfonate. This ingredient can be included as a lather boosting synthetic surfactant. It is made from coconut fatty alcohols. Equivalent synthetic surfactants can be used.
C = Sodium Alkyl Ether Sulfate. This is also a mild lather boosting synthetic surfactant.
D = Sodium Cetearyl Sulfate. This is a non-soil load filler and processing aid.
E = Sodium Soap. This is a lather booster and processing aid.
F = Magnesium Soap. This is a non-soil load filler and processing aid.
G = Fatty Acid. This is a plasticizer.
H = Paraffin. This is a plasticizer.
I = Sodium Chloride. This provides bar firmness and improves bar smear.
J = Sodium sulfate. This provides bar firmness and improves bar smear.
K = Sodium Isethionate. This provides bar firmness and improves bar smear.
L = Water. This is a binder.
M = Fragrance. This is a binder and improves odor.

The STCI bars of the present invention comprise three key ingredients: sodium topped cocoyl isethionate, plasticizing agent and binder. The corresponding high and low levels of these ingredients in functional limits are set out below in Table B.

The term "Plasticizer" as used herein means any material that is solid at room temperature, but is malleable at bar plodding processing temperatures of about 35° C. to 46° C. (95° F. to 115° F.). This is the temperature of the plasticizer. At least about 20 parts by bar weight is a plasticizer excluding any synthetic surfactant which can provide some plasticizer benefits.

The term "Binder" as used herein means any material that is by itself liquid, at room temperature and selected from water and liquid polyols. The water and liquid polyol can have a ratio of about 20:1 to 1:5; or 5:1 to 1:3 or 2:1 to 1:2.

Their levels in the bar are 3–20 parts with 3–20 parts water and zero to 15 parts polyol, etc.

TABLE B

| Key Components | | | |
|---|---|---|---|
| Key Components | High | Low | Comments |
| STCI - 10 parts to 70 parts. | Brittleness 50 parts–70 parts | Lather 10 parts–20 parts | Assumes trade-off vs. plasticizer |
| Plasticizer - comprised of a solid aliphatic materials, e.g. fatty acids, fatty alcohols, paraffins, monoglycerides, diglycerides, triglycerides, alkali soaps, alkaline soaps; or high molecular weight (solid) hydrophilic materials, e.g. polyethylene glycols, polypropylene glycols; starches, sugars and/or mixtures thereof–20 parts to 50 parts. | Lather | Brittleness | |
| Binder - includes water and low molecular weight (liquid) materials, e.g. liquid polyols | Stickiness, Smear | Brittleness, Lather | |

Referring to Table B, when the level of STCI surfactant is low, that is, from about 10 parts to about 20 parts by weight of the bar, the ratio of STCI and other lathering soaps and/or surfactants as set out in Table C is preferably from about 1:2 to about 1:8; preferably 1:3 to 1:6. This ratio is needed to provide acceptable bar lather.

Referring to Table B, when the level of sodium topped cocoyl, ($C_{12}$–$C_{18}$) isethionate (STCI) is high, that is, from about 50 parts to about 70 parts, the ratio of it to plasticizer (plastic materials) is preferably from about 2.5:1 to about 3.5:1. This ratio is needed to avoid unacceptable brittleness.

The formulation of synthetic detergent-based (syndet) bars is a delicate balancing act. There are numerous bar use properties to take into consideration: lather, messiness, economy, product pH, bar firmness, etc.

TABLE C

| Key Optional Components | High | Low |
|---|---|---|
| Mild Lathering Synthetic Surfactant - includes $C_8$ to $C_{22}$, preferably $C_{12}$ to $C_{18}$, alkyl glyceryl ether sulfonate, alkyl sulfates, betaines, sulfosuccinates, sarcosinates, taurates, glycosides, alkyl ethoxylated sulfates, etc. | Stickiness, Smear | Lather |

The STCI bar of the present invention comprises: from about 10 parts to about 70 parts lathering mild synthetic surfactant; and wherein said lathering mild synthetic surfactant is selected from topped, distilled, $C_{12}$–$C_{18}$ acyl isethionate (STCI).

It can also contain other lathering surfactants, preferably, $C_{12}$–$C_{14}$ alkyl glyceryl ether sulfonate, $C_{12}$–$C_{14}$ acyl sarcosinate, methyl acyl taurates, N-acyl glutamates, alkyl sulfosuccinates, alkyl phosphate esters, ethoxylated alkyl phosphate esters, trideceth sulfates, ethoxylated alkyl sulfates and alkyl amine oxides, betaines, sultaines, and mixtures thereof, preferably as their sodium salts; and wherein at least about 10 parts of said bar is said mild lathering, sodium topped, distilled, $C_{12}$–$C_{18}$ acyl isethionate (STCI).

It can also contain from 0 parts to 40 parts, preferably from about 4 parts to about 30 preferably from 8 parts to 20 parts, of essentially saturated long chain ($C_{15}$–$C_{22}$) alkyl synthetic surfactant selected from the group consisting of: alkyl sulfate, alkyl sarcosinate, alkyl glyceryl ether sulfonate, and mixtures thereof.

It can also contain from 0 parts to 30 parts, preferably 3 parts to 25 parts, more preferably from about 5 parts to about 20 parts of wax, preferably paraffin, having a melting point of from about 130° F./54° C. to about 180° F./82° C.

It can also contain from about 0 to 35 parts, preferably 3 parts to 25 parts, more preferably from about 5 parts to about 20 parts free fatty acid.

It can also contain from 0 parts to about 20 parts, preferably 1 parts to 15 parts, more preferably from about 2 parts to about 12 parts, sodium soap.

It can also contain from about 0 parts to about 15 parts, preferably 1–10 parts, more preferably 2–8 parts sodium isethionate.

It can also contain from 0 parts to about 5 parts, preferably 0.1 to 3 parts, more preferably 0.2–2 parts, sodium chloride.

The bar of this invention contains from about 3 parts to 20 parts, preferably 4 parts to 15 parts, more preferably from about 5 parts to 10 parts water.

The bar of this invention contains from 0 parts to about 5 parts or 0.1 to 2 parts of cationic polymer.

The bar of this invention contains from 0 parts to about 2 parts perfume, preferably 0.5 parts to 1.5 parts, more preferably, 0.8 parts to 1.2 parts.

The bar of this invention contains from 0 parts to about 50 parts, preferably 4 parts to 30 parts and more preferably from about 8 parts to 20 parts magnesium soap.

The bar of this invention contains from 0 to 5 parts, preferably 0.1 to 3 parts; more preferably 0.2–2 parts, sodium sulfate.

The bar has a pH of from about 4.0 to about 9.0, preferably 5 to 8, more preferably from about 6.5 to 7.5; and wherein said bar contains by bar weight from 20 parts–50 parts; more preferably 25 parts–45 parts; most preferably 30 parts–40 parts of plastic material selected from the group consisting of: free fatty acid, wax, sodium and magnesium soaps, other plasticizers or mixtures thereof.

The percentages, ratios, and parts herein are on a total composition weight basis, unless otherwise specified. All levels and ranges herein are approximations, unless otherwise specified. Levels of ingredients are expressed herein on a "solids" basis, incorporating all non-water components together, unless otherwise specified.

A long chain alkyl sulfate (hereinafter including its long chain equivalent synthetic surfactants). It preferably comprises $C_{16}$–$C_{18}$ alkyl chains at a level of at least about 90 parts, preferably about 93 parts, and more preferably about 97 parts. The long chain alkyl sulfate (and its equivalents) is derived from corresponding saturated straight chain alcohols. The long chain alkyl sulfate can be 100 parts $C_{16}$ to 100 parts $C_{18}$ by weight. A commercially available $C_{16}$–$C_{18}$ alkyl sulfate is SIPONR EC-111 (formerly SIPEXR EC-111), sodium cetearyl sulfate, which is approximately 60% $C_{16}$ and 36% $C_{18}$. SIPONR EC-111 is sold by Alcolac Company, Baltimore, Md. 21226. Another source is Henkel Corp., Ambler, Pa. 19002. Henkel's sodium cetearyl sulfate, LANETTE E, is an estimated 50—50% $C_{16}$–$C_{18}$ active alkyl sulfate sold as an emulsifier.

Other long chain surfactants which are equivalent to the long chain alkyl sulfate (mostly insoluble) could serve as either full or partial replacements for the long chain alkyl sulfate. Examples include long chain isethionates, sarcosinates, glyceryl ether sulfonates, etc., which have the same low solubility.

The distilled topped cocoyl isethionate of this invention is distinguished from the acyl esters of isethionic acid salts, with high levels of $C_{16}$–$C_{18}$ acyl isethionates and no more than 25% or lower $C_{14}$ acyl groups. Specifically, excluded from the present STCI bars of this invention are bars made with only stearoyl isethionate which has acyl chains of $C_{14}$ 3%; $C_{16}$ 50%; and $C_{18}$ 47%. Such bars tend to have poor lather properties.

Mild Synthetic Surfactants Defined

It is noted that surfactant mildness can be measured by a skin barrier destruction test which is used to assess the irritancy potential of surfactants. In this test the milder the surfactant, the lesser the skin barrier is destroyed. Skin barrier destruction is measured by the relative amount of radio-labeled water ($^3H$-$H_2O$) which passes from the test solution through the skin epidermis into the physiological buffer contained in the diffusate chamber. This test is described by T. J. Franz in the *J. Invest. Dermatol.*, 1975, 64, pp. 190–195; and in U.S. Pat. No. 4,673,525, Small et at., issued Jun. 16, 1987, incorporated herein by reference, and which disclose a mild alkyl glyceryl ether sulfonate (AGS) surfactant based synbar comprising a "standard" alkyl glyceryl ether sulfonate mixture. (Barrier destruction testing surprisingly shows that the long chain alkyl sulfates are milder than standard AGS.) The long chain surfactants and especially long chain alkyl sulfate preferably comprise 8 to 20 parts by weight of the bars of this invention.

The sarcosinates, and glyceryl ether sulfonates may be pure chain length variants or those derived from commercial oils such as coconut oil. Here, the lauryl chain length should preferably account for at least 20% to as much as 100% of the weight of the given mild surfactant.

A "high lathering surfactant" as defined herein, is one which lathers better than the long chain sodium $C_{16}$–$C_{18}$ alkyl sulfate.

A "mild surfactant" as defined herein is one that is milder than sodium dodecyl sulfate.

Numerous examples of other surfactants in general are disclosed in the patents incorporated herein by reference. They include limited amounts of anionic acyl sarcosinates, methyl acyl taurates, N-acyl glutamates, alkyl sulfosuccinates, alkyl phosphate esters, ethoxylated alkyl phosphate esters, trideceth sulfates, protein condensates, mixtures of ethoxylated alkyl sulfates and alkyl amine oxides, betaines, sultaines, and mixtures thereof. Included in the surfactants are the alkyl ether sulfates with 1 to 12 ethoxy groups, especially ammonium and sodium lauryl ether sulfates. Alkyl chains for these other surfactants are $C_8$–$C_{22}$, preferably $C_{10}$–$C_{18}$. Alkyl glycosides and methyl glucoside esters are preferred mild nonionics which may be mixed with other mild anionic or amphoteric surfactants in the compositions of this invention.

The bars of this invention can have from 0 to about 10 parts of high lathering, non-mild surfactants and still maintain the preferred mildness requirement of the bar. Examples of these surfactants include linear alkyl benzene sulfonates and shorter chain or traditional (coconut) alkyl sulfates.

A preferred syndet bar can contain a mixture of sodium topped distilled $C_{12}$–$C_{18}$ cocoyl isethionate (STCI) and sodium linear alkylbenzene sulfonate in a ratio of from about 35:1 to about 15:1, preferably from about 30:1 to about 20:1.

Key Plasticizers

The preferred plasticizers of the present invention are: (1) fatty acid (2) sodium soap, and (3) wax, preferably paraffin wax.

The fatty acid material which is desirably incorporated into the present invention includes material ranging in hydrocarbon chain length of from about 10 to about 22, essentially saturated. These fatty acids can be highly purified individual chain lengths and/or crude mixtures such as those derived from fats and oils. The industry term "triple pressed stearic acid" comprises about 45% stearic and 55% palmitic acids. Thus, this is its meaning as used herein.

The composition may include soaps derived from hydrocarbon chain lengths of from about 10 to about 22 (including carboxyl carbon) and are preferably saturated. It is preferred that the soap be the sodium salt, but other soluble soap can be used. Potassium, ammonium, triethanolammonium, and mixtures thereof, are deemed acceptable. The soaps are preferably prepared by in situ saponification or ion exchange with a halide salt of the corresponding fatty acids, but they may also be introduced as preformed soaps. Either some or all of the soap is preferably precomplexed with cationic polymer, or polymers, when polymer is used.

"Insoluble" soaps, e.g., magnesium and zinc soaps, are not included in the level of "sodium soap" in the composition definition. However, insoluble soaps can be used as non-lathering, non-soil-load diluents and processing aids.

The waxes are selected from the group consisting of beeswax, spermaceti, carnauba, baysberry, candelilla, montan, ozokerite, ceresin, paraffin, synthetic waxes such as Fisher-Tropsch waxes, microcrystalline wax, and mixtures thereof.

A highly preferred component of this invention is a wax, preferably paraffin wax having a melting point (M.P.) of from about 130° F. to about 180° F. (54°–82° C.), preferably from about 140° F. to about 165° F. (60°–74° C.), and most preferably from about 142° F. to about 160° F. (61°–71° C.). "High melt" paraffin is paraffin that has a melting point of about 150°–160° F. (66°–71° C.). "Low melt" paraffin is paraffin that has a melting point of about 130°–140° F. (54°–60°). A preferred paraffin wax is a fully refined petroleum wax which is odorless and tasteless and meets FDA requirements for use as coatings for food and food packages. Such paraffins are readily available commercially. A very suitable paraffin can be obtained, for example, from The National Wax Co. under the trade name 6975.

The wax, preferably paraffin, is present in the bar in an amount ranging from about 3 parts to about 30 parts by weight. The wax ingredient is used in the product to impart skin mildness, plasticity, firmness, and processability. It also provides a glossy look and smooth feel to the bar.

The Binder

This invention contains water and can contain a liquid water-soluble aliphatic polyol or polyethylene glycol or polypropylene glycol. The polyol may be saturated or contain ethylenic linkages; it must have at least two alcohol groups attached to separate carbon atoms in the chain, and must be water soluble and liquid at room temperature. If desired, the compound may have an alcohol group attached to each carbon atom in the chain. Among the compounds which are effective are ethylene glycol, propylene glycol and glycerine. A preferred polyol is dipropylene glycol, which is effective in amounts as low as 0.1 and 0.25 parts by weight, preferably 0.5 parts to about 5 parts; and more preferably from about 0.5 parts–2 parts.

Water-soluble polyethylene glycols or water-soluble polypropylene glycols useful in the present invention are those products produced by the condensation of ethylene glycol molecules or propylene glycol molecules to form high molecular weight ethers having terminal hydroxyl groups. The polyethylene glycol compounds may range from diethylene glycol to those having molecular weights as high as about 800. Normally, polyethylene glycols having molecular weights up to 800 are liquid and completely soluble in water. As the molecular weight of the polyethylene glycol increases beyond 800, they become solid and less water-soluble. The polypropylene glycol compounds useful in this invention may range from dipropylene glycol to polypropylene glycols having molecular weights of about 2000. These are normally liquid at room temperature and are readily soluble in water.

Other Ingredients

The syndet bar of this invention may comprise from 0 parts to about 5 parts, preferably from about 0.3 parts to about 1 parts, of a suitably fast hydrating cationic polymer. The polymers have molecular weights of from about 1,000 to about 5,000,000.

The cationic polymer (skin conditioning agent) is selected, e.g., from the group consisting of:

(I) cationic polysaccharides;

(II) cationic copolymers of saccharides and synthetic cationic monomers, and (III) synthetic polymers selected from the group consisting of:

(A) cationic polyalkylene imines;

(B) cationic ethoxy polyalkylene imines; and (C) cationic poly[N-[-3-(dimethylammonio)propyl]-N'-[3-(ethyleneoxyethylene dimethylammonio) propyl]urea dichloride].

Other ingredients of the present invention are selected for the various applications. E.g., perfumes can be used in formulating the skin cleansing products, generally at a level of from about 0.1 parts to about 1.5 parts of the composition. Vegetable oils, such as peanut and soybean oil can be added at levels up to 10 parts, preferably 2 to 6 parts. Alcohols, hydrotropes, colorants, and fillers such as talc, clay, calcium carbonate, oils and dextrin can also be used at appropriate levels. Preservatives, e.g., trisodium etidronate and sodium ethylenediaminetetraacetate (EDTA), generally at a level of less than 1 part of the composition, can be incorporated in the cleansing products to prevent color and odor degradation. Antibacterials can also be incorporated, usually at levels up to 1.5 parts. Salts, both organic and inorganic, can be incorporated. Examples include sodium chloride, sodium isethionate, sodium sulfate, and their equivalents.

Optional Adjunct Odor-Reducing or Odor-Controlling Materials

The compositions and articles of this invention can also contain an effective, i.e., odor-controlling, amount of various additional zeolite and non-zeolite odor-controlling materials to further expand their capacity for controlling odors, as well as the range of odor types being controlled. Such materials include, for example, cetyl pyridinium chloride, zinc chloride, EDTA, etidronate, BHT, and the like.

A preferred zeolite is substantially free of particles sized greater than 30 microns, and in fact is substantially free of particles sized over 15 microns for acceptable bar feel. "Substantially free" means that the larger particles are less than about 5 parts, preferably less than about 4 parts, more preferably less than about 3 parts, as measured by laser light scattering.

A preferred personal cleansing bar composition contains a zeolite at a level of from about 0.05 parts to about 5 parts by weight of the composition; preferably, the zeolite's $(SiO_2:Al_2O_3)Y$ molar ratio is from about 2:1 to about 50:1, said zeolite being in the protonic, sodium, potassium, ammonium, or alkylammonium form, and said composition contains 0 parts to about 0.5 parts perfume.

The following patents disclose or refer to ingredients and formulations which may be useful in the STCI bars of this invention, and are incorporated herein by reference:

| Pat. No. | Issue Date | Inventor(s) |
|---|---|---|
| 4,234,464 | 11/1980 | Morshauser |
| 4,061,602 | 12/1977 | Oberstar et al. |
| 4,472,297 | 9/1984 | Bolich et al. |
| 4,491,539 | 1/1985 | Hoskins et al. |
| 4,540,507 | 9/1985 | Grollier |
| 4,704,224 | 11/1987 | Saud |
| 4,812,253 | 3/1989 | Small et al. |
| 4,820,447 | 4/1989 | Medcalf et al. |
| 4,954,282 | 9/1990 | Rys et al. |
| 5,154,849 | 10/1992 | Visscher, et al. |

The STCI bars of this invention have a pH of from 4 to 9 in a 1 parts aqueous solution. The preferred pH is from about 5 to about 8, more preferably about 6.5 to about 7.5.

A Method of Making STCI Bars

Crutching (A, B and C are Alternative Procedures)

A.

1. If used, add melted cetearyl sulfate, and/or AGS and/or $AE_3S$ (50°–75° C.); begin agitation.
2. If used, add NaCl, then $TiO_2$, then EDTA, then etidronate, and then zeolite, and bring crutcher mixture to 85° C. under low agitation.
3. Add premeasured caustic and $Mg(OH)_2$, if used, and continue to mix slowly.
4. Steam sparge to 85° C. before adding remaining ingredients.
5. Add fatty acid and mix for 5–10 minutes at 85° C.
6. Add the paraffin, STCI, SI and continue mixing slowly for approximately 15–30 minutes while maintaining the mix temperature at 85° C.
7. If used, add glycerin and/or peanut oil slowly under constant agitation.

B.

1. Add paraffin, STCI, SI and begin agitating slowly while maintaining the temperature at 85° C.
2. If used, add molten cetearyl sulfate, and/or AGS, and/or AE3S (50°–75° C.) and maintain slow agitation and recirculation.
3. If used, add NaCl, then $TiO_2$ then EDTA, then etidronate, and then zeolite, increasing the temperature in the 85° C. range under low agitation and steam sparging.
4. Add the premeasured caustic and $Mg(OH)_2$, if used, and continue to mix slowly.
5. Add the required fatty acid and mix for another 10 minutes at 85° C. Check for uniform consistency of the crutcher batch.
6. If used, add glycerin and/or peanut oil slowly under constant agitation.

C.

1. If used, add molten cetearyl sulfate, AGS and/or $AE_3S$ (50°–75° C.) to the crutcher and begin slow agitation.

2. Add the paraffin, sodium topped, distilled cocoyl isethionate (STCI), sodium isethionate (SI) and continue to mix with agitation and begin recirculation.
3. If used, add NaCl, then $TiO_2$, then EDTA, then etidronate, and then zeolite, increasing the temperature to 85° C. while agitating and recirculating and steam sparging.
4. Add the premeasured caustic and $Mg(OH)_2$, if used, and continue to mix slowly.
5. Add the required fatty acid and mix for another 10 minutes at 85° C. Check for uniform consistency of the crutcher batch and continue to mix until fluid and lump free.
6. If used, add glycerin and/or peanut oil slowly under constant agitation.

Drying

The crutcher mix is dried and cooled using a combination flash chamber and chill roll or chill belt. The crutcher mix is first heated to approximately 265°–275° F. (130°–135° C.) by a heat exchanger and then flash dried in a chamber above the chill roll or chill belt. The chill belt or chill roll provides a uniform, thin cool (85°–95° F.; 29°–35° C.) product in flake or chip form. Typical moisture for the flake is from about 3 parts to about 15 parts, preferably from about 5 parts to about 10 parts. The way to regulate the moisture, in the order of preference, are: (1) increasing or decreasing steam pressure on the heat exchanger; (2) increasing or decreasing crutcher mix rate to the heat exchanger; and (3) increasing or decreasing crutcher mix temperature to the heat exchanger.

Amalgamating

The flakes are weighed and added to a batch amalgamator to obtain uniform flake size and a course mixture of additives that may be brought into the flake mixture (syndet or soap).

(Alternative Procedures)

A. Preweighed flakes may be amalgamated to uniform size and premeasured amounts of optional dipropylene glycol, glycerin, peanut oil and the zeolite deodorizing powder are added into the base flakes and mixed for several minutes with no perfume being added.

B. Preweighed flakes may be amalgamated to uniform size and a premeasured amount of optional dipropylene glycol, glycerin, peanut oil is added into the base flakes and admixed for several minutes before; then adding a premeasured amount of perfume. Continue amalgamating for at least one minute to thoroughly mix together the ingredients.

Milling

The 3-roll soap mills are set up with the first roll at ~120° F. (49° C.), the second roll at ~100° F. (38° C.), and the final roll at ~68° F. (20° C.). The material is passed through the mills several times to provide a homogeneous mixture of perfume and dried flakes. Typically the milled material has a temperature of 44° to 54° C.

Plodding and Stamping

The plodder is set up with the barrel temperature at about 115° F. (46° C.) and the nose temperature at 114°–122° F. (45°–50° C.). The ideal plodder is a dual stage plodder that allows use of a vacuum of about 15–25 inches (38–64 cm) of rig. The plugs should be cut in 5 inch (13 cm) sections and stamped with a cold die block using die liquor such as alcohol, if appropriate.

Laboratory Assessment of Bar

The critical bar performance attributes are smear, lather, odor and processability.

Smear Test Procedure

Equipment

1. #2-202C Fisher Brand Hexagonal Polystyrene weighing dishes (4"3").
2. #14-366A Fisher Brand Spatula.
3. Balance capable of weighing to two decimal points.
4. 120° F. (49° C.) Temperature Room.
5. Timer.

Test Method

1. Label and weigh the number of weighing dishes needed (two weighing dishes per sample, one labeled M for mush dish, one labeled S for soak dish).
2. Weigh the original bar and record the weight. Place bar in preweighed dish labeled S.
3. Add 30 mls room temperature city water to the dish containing the bar prototype (pour water down side of weighing dish). Add 30 mls room temperature city water to the dish containing the control bar. When placing the bars in the dish make sure the bars are not touching the sides of the dishes.
4. Allow bars to soak in weighing dishes at room temperature for 2 hours undisturbed.
5. After 2 hours of soaking, pick bar up carefully and allow to drain into the same dish for 15 seconds.
6. After 15 seconds, invert bar and place in preweighed dish labeled M.
7. Weigh soaked bar and record.
8. Scrape the wet surface or mush from the bar, with a spatula, into the same preweighed dish labeled M, weigh and record, this is the "wet smear" grade. Let the mush and soak water dry overnight, weigh and record. This is the "dry smear" grade. Best results for scraping are seen when the spatula is held loose in hand being careful not to gouge the bar or to scrape too deeply. When the surface of the bar no longer appears to look wet or shiny, scraping is completed. To eliminate variability of scraping from person to person, results from each test will be reported relative to the control placed in that test.

All series of testing should include control, and all samples should be run in duplicates. A maximum of 7 products (6 plus a control) can be tested at one time, and an interval of 10 minutes between every 4 samples should be allotted for the addition of water as to not allow any products a lag time for soaking longer than 2 hours.

Bar Soap Handwash Lather Volume Test

The handwash lather test is used to provide in-use lather volume measurements for the lather performance of skin cleansing bars. The test measures both the ultimate lather volume generated and the volume which is generated after a very short lathering period (to reflect lathering ease). The lather volumes are generated under soil-loaded conditions.

Synthetic soil is used for the soil-loaded lather volume test reported in the literature; see Small, et al., supra.

Grading Scale

Soil Loaded

7—Exceptional
6—Very much higher than target
5—Higher than target (See Example 3)
4—Target volume (See C.E. 1)
3—Slightly lower than target
2—Lower than target

Odor Evaluation

Samples to be graded are placed in clean 12 oz. (341 ml.) paper cups with corresponding lids. A standard bar of the same composition as the sample is placed in a similar cup. Bars are aged at least 24 hours before grading.

The order of grading multiple bar soap versions is as follows: perfume-free standards and samples first; low perfume impact bar standards and samples next; higher perfume impact bars last. The procedure of evaluation is to compare the sample product against a standard quality bar of known quality and grade. Differences in perfume impact, character and base notes are evaluated with each test. Perfume-free bars are compared to a standard of "good" quality and grades given are good, fair or poor, by trained observers. Perfumed products are graded on a scale of 1–10 with the high standard quality bar having a grade of 9.0. Wet grades are evaluated with the same appropriate scale as the neat grades. A wet grade is performed by washing with the bar, paying close attention to the lather odor and the bar odor itself.

Assessment of Processability: The Mill Test

Mill Test Procedure

1. A standard three-roll mill is employed with the take-up roll set at 120° F. (48° C.), the transfer roll at 110° F. (43° C.) and the discharge roll at 80° F. (26° C.).
2. Final flake thickness is about 0.010 inches.
3. After the third mill pass, the material is evaluated as described below.

Mill Grade Assessment (See Examples Herein)

| Grade | Product Flake Appearance Coming Off Mill |
|---|---|
| 10 | Like Standard Soap (50/50 T/C) |
| 9 | Non-Sticky; less than four compaction layers; no build-up. (See Example 5) |
| 8 | Non-Sticky; less than four compaction layers; 0.010" (0.25 millimeters) build-up. |
| 7 | Slightly sticky; about eight compaction layers; 0.010"–0.016" build-up (See Example 3) |
| 6 | Slightly sticky; large chunks; bridging; >0.016" build-up. (See EE. 4) |
| 5 | More sticky; sheeting; >0.016" build-up. |
| 4 | Increasing stickiness; sheeting; bridging; dough-like; high build-up. |
| 1–3 | Extremely sticky; very difficult to process. |

Mill Force Assessment of Processability

As the material is removed from the discharge roll it impacts a sheet metal plate so that the 0.010 inch (0.25 millimeters) thick sheet of material gathers into compressed chunks. The force which the material exerts on the sheet metal plate is an indication of the cohesiveness and brittleness of the material. This force is recorded as the mill force gauge reading. A more cohesive, less brittle material is less processable on typical bar-making equipment. A large force gauge reading indicates a more cohesive, less brittle and therefore, a less processable formula.

Examples and Formulas

The following examples and formulas are illustrative and are not intended to limit the scope of the invention. The methods of making milled bars are well known. All levels and ranges, temperatures, results, etc. used herein are approximations unless otherwise specified. Therefore, the percentages do not necessarily add up to 100 parts. All component levels are percentages based on weight.

Comparative Example 1 (C.E. 1) vs. Examples 2 and 3

These examples illustrate the ability to achieve better lather, better odor and higher moisture content without jeopardizing mildness and processability via replacing regular coconut acyl isethionate with sodium topped distilled coconut acyl isethionate (see Tables 1A–1C). High Melt Point Paraffin melts at about 158° F. (70° C.). Low Melt Point Paraffin melts at about 131° F. (55° C.).

TABLE 1A

| Component | C.E. 1 | Ex. 2 | Ex. 3 |
|---|---|---|---|
| Regular Na-Cocoyl Isethionate | 47 | | |
| Na-Topped Cocoyl Isethionate (STCI) | | 45 | 45 |
| Na-Cetearyl Sulfate | 9 | 9 | 9 |
| Na-soap** | 4 | 4 | 4 |
| Free Fatty Acid** | 10 | 9 | 9 |
| Paraffin - Low Melt Point | | | 9 |
| Paraffin - High Melt Point | 9 | 9 | |
| NaCl | 0.5 | 0.5 | 0.5 |
| Na2SO4 | 1 | 1 | 1 |
| Na-Isethionate | 6 | 5 | 5 |
| Water | 6 | 10 | 10 |
| Fragrance | 1 | 1 | 1 |
| Miscellaneous* | Balance | Balance | Balance |
| Total Parts = 100 | | | |

*NA - not available. Miscellaneous includes unreacted feedstocks and products of secondary side reactions. See Table 1B for the chainlengths of the acyl isethionates.

TABLE 1B

| | C.E. 1 | Ex. 2 | Ex. 3 |
|---|---|---|---|
| Chainlengths of Acyl Isethionates: | | | |
| $C_8$ | 8 | 0 | 0 |
| $C_{10}$ | 7 | 0 | 0 |
| $C_{12}$ | 53 | 60 | 60 |
| $C_{14}$ | 17 | 23 | 23 |
| $C_{16}$ | 7 | 10 | 10 |
| $C_{18}$ | 4 | 7 | 7 |
| $C_{18:1}$ | 3 | 1 | 1 |
| Total Isethionate | 100 | 100 | 100 |

**Soap and Fatty Acid Chainlengths:
The Na -soap, and fatty acid chainlengths in C.E. 1 are representative of a blend of about 15 parts coconut, 15 parts lauric, 6 parts myristic and 64 parts triple pressed stearic acid or salts thereof. Ex. 2 and Ex. 3 are representative of a blend of about 5 parts coconut, 46 parts lauric, 16 parts myristic and 33 parts triple pressed stearic acid or salts thereof.

The bar characteristics are set out in Table 1C.

TABLE 1C

| | C.E. 1 | Ex. 2 | Ex. 3 |
|---|---|---|---|
| Processability | | | |
| Mill Grade | 8.5 | 8 | 7 |
| Mill Force Gauge - lbs. force | 2 | 2 | 0 |
| Bar Performance - Smear | | | |
| Wet Mush Smear | 0.7 | 0.5 | 0.7 |
| Dry Mush Smear | 0.9 | 0.7 | 0.8 |
| Bar Performance - Lather | | | |
| Flash Soil Lather | 3.5 | 3.5 | 4.5 |
| Ultimate Soil Lather | 4 | 4.5 | 5.5 |
| Odor | 7.5 | 8.5 | 8.5 |

Comparative Example 1 (C.E. 1) is a state of the art bar. Its acyl isethionate chainlength is based on a typical coconut fatty acid feedstock. With the presence of about 15% $C_8$ and $C_{10}$ isethionate, C.E. 1 is limited to about 6 parts moisture as it gets unacceptably soft and sticky on the mill at moistures of about 8 parts.

Examples 2 and 3 are acyl isethionate based personal cleansing bars that are based on the sodium topped coconut acyl isethionate. Neither Example contains over 0.5 parts $C_8$ or $C_{10}$ acyl isethionate. These Examples are similar in composition to C.E. 1 but have up to 10 parts moisture and maintain acceptable processability. While not being bound to any theory, it is theorized that this higher moisture improves bar lather.

Comparative Example 1 received an odor grade of 7.5. This is an acceptable odor grade. However, Examples 2 and 3, which have the topped distilled, cocoyl isethionate, received unexpected and surprising higher (better) odor grades of 8.5.

Example 3, based on its processability (7/0), its outstanding lathers (4.5/5.5) and its outstanding odor grade (8.5) is the best mode example. A preferred bar is similar to Example 3 but with 0.5 parts to 1.5 parts polymer.

Experimental Example 4 (E.E.4) vs. Example 5

These examples illustrate the ability to add hygroscopic lather boosting synthetic surfactant(s) without jeopardizing processability by using topped coconut acyl isethionate.

TABLE 2A

| Component | E.E. 4 | Ex. 5 |
|---|---|---|
| Regular Na-Cocoyl Isethionate | 44 | |
| Na-Topped Cocoyl Isethionate (STCI) | | 44 |
| Na-Laureth Sulfate (AE3S) | 4 | 4 |
| Na-soap** | 4 | 4 |
| Mg-soap** | 8 | 8 |
| Fatty Acid** | 10 | 10 |
| Paraffin - High Melt Point | 9 | 9 |
| NaCl | 0.5 | 0.5 |
| Na2SO4 | 1 | 1 |
| Na-Isethionate | 5 | 5 |
| Water | 6 | 6 |
| Fragrance | 0.3 | 0.3 |
| Miscellaneous* | Balance | Balance |
| Total Parts = 100 | | |

*Miscellaneous includes unreacted feedstocks and products of secondary side reactions.

TABLE 2B

| | E.E. 4 | Ex. 5 |
|---|---|---|
| Acyl Isethionate Chainlengths: | | |
| $C_8$ | 8 | 0 |
| $C_{10}$ | 7 | 0 |
| $C_{12}$ | 53 | 60 |
| $C_{14}$ | 17 | 23 |
| $C_{16}$ | 7 | 10 |
| $C_{18}$ | 4 | 7 |
| $C_{18:1}$ | 3 | 1 |
| Total Isethionate | 100 | 100 |

**Soap and Fatty Acid Chainlengths:
Na-soap, Mg-soap and fatty acid used in E.E. 4 and Ex. 5 comprise: about 10 parts coconut, 20 parts lauric, 5 parts myristic and 65 parts of triple pressed stearic acid or the salts thereof.

TABLE 2C

| | E.E. 4 | Ex. 5 |
|---|---|---|
| Processability | | |
| Mill Grade | 6 | 9.5 |
| Mill Force Gauge - lbs. force | NA | NA |
| Bar Performance - Smear | | |
| Wet Mush Smear | 1.0 | 0.8 |
| Dry Mush Smear | NA | NA |
| Bar Performance - Lather | | |
| Flash Soil Lather | 3.5 | 3.5 |
| Ultimate Soil Lather | 4.5 | 4.5 |

NA - not available

Experimental Example 4 (E.E. 4) has an acyl isethionate chainlength based on a typical coconut fatty acid feedstock comprising 15% $C_8$ and $C_{10}$. It additionally contains sodium laureth sulfate ($AE_3S$) and magnesium soap. $AE_3S$ is known to make personal cleansing bars sticky and difficult to process due to the high levels of unreacted alcohol that are introduced with the $AE_3S$ paste. E.E. 4 has better lather than the state of the art bar C.E. 1 (3.5/4.5 vs. 3.5/4.0). However, the processability of the E.E.4 is unacceptable based on its mill grade of only 6.

Example 5 is similar in composition to E.E. 4 but is made with topped coconut isethionate (STCI) having about 1% $C_8$, $C_{10}$, $C_{18:1}$ and $C_{18:2}$ SCI. Its processability is significantly better than E.E. 4 based on its higher mill grade of 9.5. Example 5, of this invention, maintains the very good lather grades of 3.5/4.5.

Examples 6 and 7

These examples illustrate the ability to add larger amounts of liquid ingredients such as 8 parts glycerin and/or 4 parts vegetable oils, e.g., soy or peanut oil to syndet bars in addition to a large amount of hygroscopic lather boosting synthetic surfactants like 16 parts sodium alkyl (cocoyl) glyceryl ether sulfonate (AGS). Comparable bars made with regular sodium cocoyl isethionate are unacceptably soft and sticky.

TABLE 3A

| Component | Ex. 6 | Ex. 7 |
|---|---|---|
| Na-Topped Cocoyl Isethionate | 28 | 29 |
| Na-Alkyl Glyceryl Ether Sulfonate (AGS) | 16 | 16 |
| Na-soap** | 4 | 4 |
| Mg-soap** | 9 | 9 |
| Fatty Acid** | 9 | 10 |
| Glycerin | 8 | |
| Peanut Oil | | 4 |
| Paraffin - Low Melt Point | 9 | 9 |
| NaCl | 0.5 | 0.5 |
| Na2SO4 | 1 | 1 |
| Na-Isethionate | 3 | 3 |
| Water | 5 | 5 |
| Fragrance | 1 | 1 |
| Miscellaneous* | Balance | Balance |
| Total Parts = 100 | | |

*Miscellaneous includes unreacted feedstocks and products of secondary side reactions.

TABLE 3B

| Component | Ex. 6 | Ex. 7 |
|---|---|---|
| Acyl Isethionate Chainlengths: | | |
| $C_8$ | 0 | 0 |
| $C_{10}$ | 0 | 0 |
| $C_{12}$ | 60 | 60 |
| $C_{14}$ | 23 | 23 |
| $C_{16}$ | 10 | 10 |
| $C_{18}$ | 7 | 7 |
| $C_{18:1}$ | 1 | 1 |
| Total Isethionate | 100 | 100 |

**Soap and Fatty Acid Chainlengths:
The Na-soap, Mg-soap and fatty acid chainlengths are representative of a blend of about 7 parts coconut, 25 parts lauric, 6 parts myristic, and 62 parts triple pressed stearic acid of salts thereof.

TABLE 3C

| | Ex. 6 | Ex. 7 |
|---|---|---|
| Processability | | |
| Mill Grade | 7.5 | 7 |
| Mill Force Gauge - lbs. force | 7 | 8 |
| Bar Performance - Smear | | |
| Wet Mush Smear | 1.3 | 1.3 |
| Dry Mush Smear | 1.5 | 1.6 |
| Bar Performance - Lather | | |
| Flash Soil Lather | 2 | 3.5 |
| Ultimate Soil Lather | 3.5 | 4.5 |
| Odor | 6 | 6.5 |

Example 6 and 7 are both STCI-based bar compositions. They contain high levels of AGS. Despite the 16 parts AGS, acceptable processability was maintained. The 8 parts glycerine in Example 6 and the 4 parts peanut oil in Example 7 should be noted. The processability of Examples 6 and 7 are respectively 7.5/7 and 7/8. The lower odor grades (6 and 6.5) of these examples are a result of impurities in the particular AGS that was used. These examples are less preferred because of the low odor grades.

Comparative Example 1 is a comparative to Examples 2 and 3. Experimental Example 4 is comparative to Example 5. Examples 6 and 7 are alternative formulations of this invention. The STCI bars are improvements over comparable bars made with regular cocoyl isethionate. The STCI improvements provide one or more of the following advantages: improved processability; improved odor; improved color stability; and/or improved lather.

What is claimed is:

1. A personal cleansing bar composition comprising:

A. from about 10 parts to about 70 parts of sodium distilled, topped cocoyl isethionate wherein said sodium distilled, topped cocoyl isethionate has the following mixture of acyl groups:

i.) from about 45% to about 65% $C_{12}$;

ii.) from about 30% to about 55% $C_{14}$, $C_{16}$ and $C_{18}$; and iii.) from about zero to about 4% combined $C_8$ and $C_{10}$ acyl groups;

B. from about 3 parts to about 20 parts of a binder; and

C. from about 20 parts to about 50 parts of a plasticizer.

2. A personal cleansing bar composition in accordance to claim 1 comprising by bar weight:

A. from about 10 parts to about 70 parts of said sodium distilled, topped cocoyl isethionate B. from 0 parts to about 40 parts of essentially saturated long, chain ($C_{15}$–$C_{22}$ alkyl) synthetic surfactant selected from the group consisting of: alkyl sulfate, alkyl sarcosinate, alkyl glyceryl ether sulfonate, and mixtures thereof;

C. from 0 parts to about 30 parts of a wax having a melting point of from about 130° F./54° C. to about 180° F./82° C.;

D. from 0 parts to about 60 parts lathering mild synthetic surfactant; and wherein said lathering mild synthetic surfactant is selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates, ethoxylated alkyl amine oxides, betaines, sultaines, $C_{12}$–$C_{14}$ alkyl glyceryl ether sulfonate, $C_{12}$–$C_{18}$ acyl sarcosinate, and mixtures thereof;

E. from 0 parts to about 35 parts fatty acid;

F. from 0 parts to about 20 parts sodium soap;

G. from 0 parts to about 15 parts sodium isethionate;

H. from 0 parts to about 5 parts sodium chloride;

I. from 3 parts to about 20 parts said water;

J. from 0 parts to about 5 parts of a polymer;

K. from 0 parts to about 2 parts perfume;

L. from 0 parts to about 5 parts disodium sulfate; and

M. from 0 parts to about 50 parts magnesium soap;

wherein when said sodium distilled, topped cocoyl isethionate (A) level is at about 15 parts to about 60 parts; said lathering mild synthetic surfactant (D) is from about 20 parts to about 60 parts; and wherein said personal cleansing bar composition contains at least about 20 parts of a plasticizer selected from the group consisting of said (F) sodium soap, (E) fatty acid or (C) wax or mixtures thereof.

3. A personal cleansing bar composition according to claim 2 comprising from about 10 parts to about 40 parts of said lathering surfactant (D); about 4 parts to about 15 parts water; and from about 20 parts to about 50 parts of said sodium distilled, topped cocoyl isethionate (A).

4. A personal cleansing bar composition according to claim 2 wherein the lathering synthetic surfactant (D) is selected from the group consisting of: alkyl ether sulfates, alkyl glyceryl ether sulfonate, acyl sarcosinate, and mixtures thereof.

5. The bar of claim 2 wherein said bar contains about 3 parts to about 20 parts of a binder wherein the binder comprises water.

6. The bar of claim 2 wherein said bar contains from 20 parts to 50 parts of a (non-synthetic surfactant) plasticizer which is solid at room temperature and malleable at 95° F. to 115° F. (35° C. to 46° C.) in the bar formula.

7. A personal cleansing bar composition according to claim 2 wherein the wax is selected from the group consisting of beeswax, spermaceti, carnauba, baysberry, candelilla, montan, ozokerite, ceresin, paraffin, synthetic waxes such as microcrystalline wax, and mixtures thereof.

8. A personal cleansing bar composition according to claim 2 wherein the polymer level is 0.3–1 parts and is selected from the group consisting of: cationic polymer, anionic polymer, zwitterionic polymer, and mixtures thereof.

9. A personal cleansing bar composition in accordance to claim 1 comprising:

A. from about 15 parts to about 60 parts of said sodium distilled, topped cocoyl isethionate;

B. from about 3 parts to about 25 parts of paraffin wax having a melting point of from about 130° F./54° C. to about 180° F./82° C.;

C. from about 15 parts to about 50 parts lathering mild synthetic surfactant; and wherein said lathering mild synthetic surfactant is selected from the group consisting of methyl acyl taurates, N-acyl glutamates, alkyl sulfosuccinates, alkyl phosphate esters, ethoxylated alkyl phosphate esters, trideceth sulfates, ethoxylated alkyl sulfates, ethoxylated alkyl amine oxides, betaines, sultaines, $C_{12}$–$C_{14}$ alkyl glyceryl ether sulfonate, $C_{12}$–$C_{18}$ acyl sarcosinate, and mixtures thereof;

D. from about 3 parts to about 25 parts fatty acid;

E. from about 1 part to about 15 parts sodium soap;

F. from about 4 parts to about 30 parts magnesium soap;

G. from about 1 part to about 10 parts sodium isethionate;

H. from about 0.1 part to about 3 parts sodium chloride;

I. from about 4 parts to about 15 parts said water;

J. from 0 parts to about 5 parts of a cationic polymer; and

K. from about 0.5 parts to about 1.5 parts perfume;

wherein said personal cleansing bar composition has a pH of from about 4.0 to about 9.0; and wherein said personal cleansing bar composition contains at least about 20 parts of a plasticizer selected from the group consisting of said sodium soap, magnesium soap, fatty acid or wax or mixtures thereof.

10. A personal cleansing bar composition according to claim 9 wherein said bar contains: 20–50 parts (A); 5–20 parts (B); 15–30 parts (C); 5–20 parts (D); 2–12 parts (E); 8–20 parts (F); 2–8 parts (G); 0.2–2 parts (H); 5–10 parts (I); 0 to 1.5 parts (J); and about 0.8 parts to 1.2 parts (K); and wherein said bar has a pH of about 6.5 to about 7.5.

11. A personal cleansing bar composition according to claim 9 wherein said lathering synthetic surfactant (C) is a mixture of said $C_{12}$–$C_{14}$ alkyl glyceryl sulfonate and said ethoxylate (3) alkyl sulfate.

* * * * *